United States Patent [19]

Mantegani et al.

[11] 4,252,941
[45] Feb. 24, 1981

[54] ERGOT DERIVATIVES

[75] Inventors: Sergio Mantegani; Giuliana Arcari; Anna M. Caravaggi; Germano Bosisio, all of Milan, Italy

[73] Assignee: Farmitalia Carlo Erba S.p.A., Milan, Italy

[21] Appl. No.: 72,289

[22] Filed: Sep. 4, 1979

[30] Foreign Application Priority Data

Sep. 8, 1978 [GB] United Kingdom ............... 36080/78

[51] Int. Cl.$^3$ .......................................... C07D 457/02
[52] U.S. Cl. .................................. 544/125; 544/361; 546/67; 424/248.5; 424/248.52; 424/248.57; 424/250; 424/261
[58] Field of Search .................... 546/67; 544/125, 361

[56] References Cited

U.S. PATENT DOCUMENTS

| 3,985,752 | 10/1976 | Kornfeld et al. | 546/67 |
| 4,064,130 | 12/1977 | Semonsky et al. | 546/67 |
| 4,166,911 | 9/1979 | Bernardi et al. | 546/67 |

OTHER PUBLICATIONS

Krepelka et al., Coll. Czech. Chem. Commun., vol. 42, p. 1209–1212 (1977).
Bernardi et al., "Il Farmerco"; No. 10, pp. 789–795, (10/1975).

Primary Examiner—Mary C. Lee
Attorney, Agent, or Firm—Stevens, Davis, Miller & Mosher

[57] ABSTRACT

Compounds and process for making same are disclosed, the compounds having the formula (I):

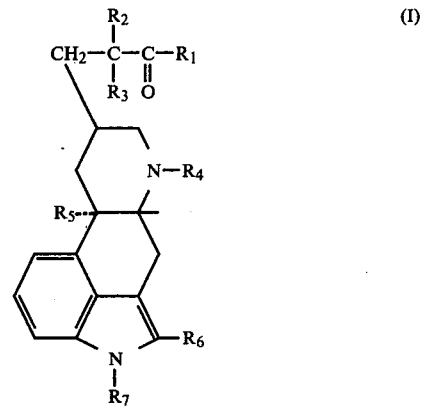

wherein $R_1$ represents a methyl, phenyl, piperidino, 1-pyrrolidinyl, morpholino or 4-methyl-1-piperazinyl group, an alkyl or alkoxy group having from 1 to 4 carbon atoms, an amino group, a substituted amino group of the formula NHR' (wherein R' represents an alkyl group having from 1 to 4 carbon atoms, a cycloalkyl group, a benzyl group, or a phenyl group) or a substituted amino group of the formula NR" R''' (wherein R" and R''' both represent alkyl groups having from 1 to 4 carbon atoms);

$R_2$ represents a hydrogen atom, an alkyl group having from 1 to 4 carbon atoms, or a phenyl group;

$R_3$ represents a fluorine atom, a cyano, difluoromethyl, difluorobromomethyl, trifluoromethyl, methylthio, methylsulphonyl, or sulphonamido group, an alkoxy group having from 1 to 4 carbon atoms, an acyl group having from 2 to 4 carbon atoms, or a benzoyl group;

$R_4$ represents a hydrocarbon group having from 1 to 4 carbon atoms;

$R_5$ represents a hydrogen atom or a methoxy group;

$R_6$ represents a hydrogen or halogen atom or a methyl group; and $R_7$ represents a hydrogen atom or a methyl group.

The 2-cyano derivatives are especially preferred.

30 Claims, No Drawings

ERGOT DERIVATIVES

This invention relates to ergoline derivatives and processes for their preparation.

The invention provides ergoline derivatives of the general formula (I):

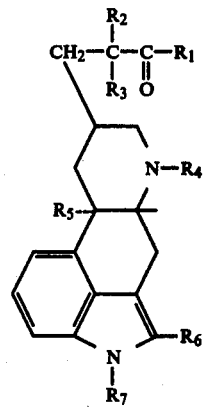

wherein $R_1$ represents a methyl, phenyl, piperidino, 1-pyrrolidinyl, morpholino or 4-methyl-1-piperazinyl group, an alkyl or alkoxy group having from 1 to 4 carbon atoms, an amino group, a substituted amino group of the formula NHR' (wherein R' represents an alkyl group having from 1 to 4 carbon atoms, a cycloalkyl group, a benzyl group, or a phenyl group) or a substituted amino group of the formula NR"R''' (wherein R' and R''' both represent alkyl groups having from 1 to 4 carbon atoms);

$R_2$ represents a hydrogen atom, an alkyl group having from 1 to 4 carbon atoms, or a phenyl group;

$R_3$ represents a fluorine atom, a cyano, difluoromethyl, difluorobromomethyl, trifluoromethyl, methylthio, methylsulphonyl, or sulphonamido group, an alkoxy group having from 1 to 4 carbon atoms, a acyl group having from 2 to 5 carbon atoms, or a benzoyl group;

$R_4$ represents a hydrocarbon group having from 1 to 4 carbon atoms;

$R_5$ represents a hydrogen atom or a methoxy group;

$R_6$ represents a hydrogen or halogen atom or a methyl group; and $R_7$ represents a hydrogen atom or a methyl group.

Ergoline derivatives of the general formula (I) as above defined may be prepared by condensing a compound of the general formula (II) below with an alkaline salt of a compound of the general formula (III) below. In the general formulae (II) and (III), $R_1$, $R_2$, $R_3$, $R_4$, $R_5$, $R_6$ and $R_7$ have the meanings given above.

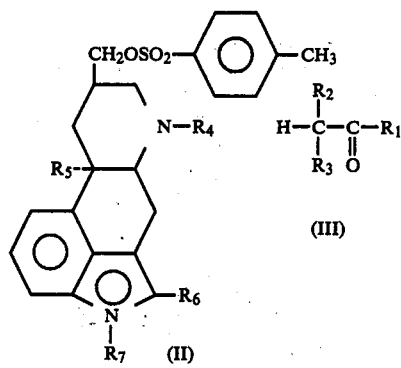

The condensation process, which is also within the scope of the invention, is carried out in a polar aprotic solvent at a temperature of from 50° to 100° C. for 2 to 10 hours. Suitable polar aprotic solvents are dimethylsulphoxide, dimethylformamide.

The condensation is preferably carried out in the presence of sodium or potassium iodide. The condensation products may be purified by conventional procedures. Chromatography over silica gel is especially suitable.

Compounds according to this invention are useful as antihypertensive agents and also have moderate to good antiprolactinic activity.

EVALUATION OF ANTI-HYPERTENSIVE ACTIVITY

1. Spontaneously Hypertensive Rat (MHS)

Four spontaneously hypertensive male rats, strain MHS, weighing 250–300 g for each group were used. The animals were treated for four consecutive days. The drugs were administered by gastric gavage while suspended in 5% arabic gum (0.2 ml/100 g body weight), and blood pressure (BP) and heart rate (HR) were measured at the tail by BP Recorder W+W. Blood pressure and heart rate were measured on the first and fourth day of treatment 1 hour before and 1 and 5 hours after drug administration. Results are reported in Tables 1 and 2.

2. Normotensive Rat (NR)

Blood pressure recordings have been made in conscious normotensive unrestrained rats weighing approximately 300 g, via a catheter cronically inserted into the left common carotid artery. Implantation of arterial cannula was made under sodium pentobarbital anaesthesia (50 mg/kp i.p.) A 1 cm long incision was made through the previously shaved ventral surface of the neck and the tissues overlying the trachea parted by blunt dissection to reveal the carotid artery. The polyethylene catheter used was made with PE 50 tubing, previously filled with saline containing 250 I.U./ml heparin. The tip of the cannula was pushed at least 2 cm inside the vessel toward the heart. The cannula was then firmly tied and passed beneath the skin to emerge from a small incision in the back of the neck. During the postoperative period and before the start of each recording session, the cannula was flushed through daily with saline containing heparin (250 I.U./ml). The experiments were performed two days after surgery. Drugs were administered by gastric gavage. Results are reported in Tables 3 and 4.

EVALUATION OF THE TOXICITY (LD₅₀)

Ten male mice for each group were orally treated with drugs at different dose levels for the determination of lethal dose 50 ($LD_{50}$). Mice were observed for seven days after administration. $LD_{50}$'s are summarized in Table 5.

TABLE 1

Variation in Blood Pressure in MHS Rats

| Compound | Dose mg/kg os | First Day Change in BP (mm Hg) | | Fourth Day Change in BP (mm Hg) | |
|---|---|---|---|---|---|
| | | 1 h after dose | 5 hs after dose | 1 h after dose | 5 hs after dose |
| 355/1057 | 2 | −25 | 0 | −26 | −31 |
| | 5 | −51 | −41 | −45 | −31 |
| 1131 | 2 | −26 | − 9 | −22 | −25 |
| | 5 | −48 | −43 | −17 | −16 |
| 1133 | 2 | −20 | −11 | −21 | −10 |
| | 5 | −24 | − 9 | −42 | −25 |
| 1138 | 2 | −23 | −14 | −30 | −15 |
| | 5 | −25 | − 9 | −26 | −11 |
| 1139 | 2 | −13 | −23 | −18 | −12 |
| | 5 | −25 | −24 | −12 | −13 |
| Hydralazine | 2 | + 2 | +18 | + 7 | + 5 |
| | 5 | −52 | −38 | − 7 | − 8 |
| α-methyl-DOPA | 30 | − 3 | −12 | −12 | −19 |
| | 100 | + 5 | −38 | −41 | −53 |

TABLE 2

Variation in Heart Rate in MHS Rats

| Compound | Dose mg/kg os | First Day Change in HR (b/min) | | Fourth Day Change in HR (b/min) | |
|---|---|---|---|---|---|
| | | 1 h after dose | 5 hs after dose | 1 h after dose | 5 hs after dose |
| 355/1057 | 2 | 0 | − 8 | − 2 | − 5 |
| | 5 | + 5 | +35 | +25 | +20 |
| 1131 | 2 | −20 | + 5 | −55 | + 5 |
| | 5 | −18 | +10 | −18 | + 7 |
| 1133 | 2 | −33 | −28 | −20 | − 3 |
| | 5 | 0 | +13 | −13 | − 8 |
| 1138 | 2 | −25 | −10 | −47 | −12 |
| | 5 | − 8 | + 5 | −20 | −25 |
| 1139 | 2 | + 7 | +12 | +47 | +35 |
| | 5 | +28 | +13 | −10 | −12 |
| Hydralazine | 2 | +10 | −28 | +43 | +23 |
| | 5 | −45 | +12 | +10 | +12 |
| α-methyl-DOPA | 30 | +40 | +15 | +57 | −18 |
| | 100 | +87 | +65 | +77 | +37 |

TABLE 3

Variation in Blood Pressure in NR Rats

| Compound | Dose mg/kg os | Change (mm Hg) in Blood Pressure after Treatment | | | | | | |
|---|---|---|---|---|---|---|---|---|
| | | 30' | 60' | 120' | 180' | 240' | 360' | 24h |
| 355/1057 | 5 | −23 | −23 | −22 | −21.7 | −23 | −20 | −12 |
| 1131 | 5 | −22 | −22 | −23 | −20 | −19 | −10 | 0 |
| 1133 | 5 | −15 | −20 | −15 | −10 | − 9 | 0 | + 5 |
| 1138 | 5 | −10 | −20 | −15 | −10 | −10 | 0 | 0 |
| 1139 | 5 | − 5 | −12 | −12 | −10 | − 5 | 0 | + 2 |
| Hydralazine | 5 | −19 | −13 | −10 | − 7 | − 5 | − 7 | 0 |

TABLE 4

Variation in Heart Rate in NR Rats

| Compound | Dose mg/kg os | Change (b/min) in heart rate after treatment | | | | | | |
|---|---|---|---|---|---|---|---|---|
| | | 30' | 60' | 120' | 180' | 240' | 360' | 24h |
| 355/1057 | 5 | −25 | −40 | −42 | −22 | +10 | + 3 | + 6 |
| 1131 | 5 | −20 | −30 | −20 | −20 | −10 | +10 | +10 |
| 1133 | 5 | −25 | −45 | −40 | −40 | −10 | − 5 | 0 |
| 1138 | 5 | −15 | −30 | −30 | −15 | 0 | + 5 | +10 |
| 1139 | 5 | 0 | +10 | +10 | − 5 | 0 | +15 | 0 |
| Hydralazine | 5 | +70 | +40 | +21 | + 9 | +21 | +12 | + 3 |

TABLE 5

Acute Toxicity $LD_{50}$'s in Mice (mg/kg per os)

| | |
|---|---|
| 355/1057 | >1000 |
| 1131 | >1000 |
| 1133 | 500 |
| 1138 | 500 |
| 1139 | 125 |
| Hydralazine | 122 |
| α-methyl-DOPA | 5300 |

From the data reported in Table 1 it is apparent that compounds according to the invention induce a consistent blood pressure fall in spontaneously hypertensive rats both at 2 and 5 mg/kg os. This reduction of the blood pressure appears not only on the first day of treatment but also on the fourth day showing absence of tachyphylaxis. Moreover the reduction lasts 5 hours at least. When compared with hydralazine and α-methyl-DOPA, two known antihypertensive drugs, the new compounds, at the 2 mg/kg level, are more active than hydralazine and more than 15 fold as active as α-methyl-DOPA. At 5 mg/kg level the new compounds are more active than hydralazine, particularly on the fourth day, and more than 20 fold as active as α-methyl-DOPA. When the variation of the heart rate (HR) is considered, it can be seen (Table 2) that the new compounds induce only minor variations whereas α-methyl-DOPA greatly increases it, particularly at the 5 mg/kg level.

The results obtained in the incannulated normotensive rat (Table 3) confirm the antihypertensive activity of the new compounds which compare favorably with that of hydralizine. Moreover, the variations of the heart rate (Table 4) are limited and in any case a favorable reduction rather than an unfavorable increase in the heart rate is observed. Finally the toxicity of the new compounds, expressed as $LD_{50}$ (Table 5), is no greater than that of hydralazine, being in many cases substantially less, and when the therapeutic ratio (activity versus toxicity) is considered, the new compounds appear to be largely better antihypertensive agents than α-methyl-DOPA.

EXAMPLE 1

2-Cyano-3-(6'-methylergoline-8'β)propionic acid ethyl ester (I: $R_1=OCH_2CH_3$, $R_3=CN$, $R_4=CH_3$, $R_2=R_5=R_6=R_7=H$).

A mixture of 16.9 g of sodium ethyl cyanoacetate, 41 g of 6-methyl-8β-tosyloxymethylergoline and 16 g of potassium iodide in 250 ml of dimethylsulphoxide and 50 ml of ethyl cyanoacetate was heated under stirring at 70° C. for 5 hours. The solution was poured into 7 liters of iced water, and the resultant precipitate was filtered off, dried and chromatographed on a silica gel column, using chloroform as eluent, to give 24 g of the title compound, m.p. 200°–202° C.

EXAMPLE 2

2-Cyano-3-(6'-methylergoline-8'β)-N-propionylmorpholine (I: $R_1$=morpholino, $R_3$=CN, $R_4$=CH$_3$, $R_2$=$R_5$=$R_6$=$R_7$=H)

A mixture of 0.85 g of sodium cyanoacetylmorpholine, 2 g of 6-methyl-8β-tosyloxymethylergoline, 0.6 g of sodium iodide in 10 ml of dimethylsulphoxide and 2 g of cyanoacetylmorpholine was heated under stirring at 80° C. for 10 hours. The solution was poured into 500 ml of water and the resultant precipitate was filtered off, dried and chromatographed over silica gel to give 1.7 g of the title compound, m.p. 220°–221° C.

EXAMPLE 3

2-Cyano-3-(6'-methylergoline-8'β)-N-phenylpropionamide (I: $R_1$=anilino, $R_3$=CN, $R_4$=CH$_3$, $R_2$=$R_5$=$R_6$=$R_7$=H)

Operating as in Example 2, but employing sodium cyanoacetanilide, 2-cyano-3-(6'-methylergoline-8'β)-N-phenylpropionamide, m.p. 180°–181° C., was obtained in 60% yield.

EXAMPLE 4

2-Cyano-3-(6'-methylergoline-8'β)-N-propionyl(N'-methyl) piperazine (I: $R_1$=4-methyl-1-piperazinyl, $R_3$=CN, $R_4$=CH$_3$ $R_2$=$R_5$=$R_6$=$R_7$=H)

Operating as in Example 2, but employing sodium cyanoacetyl-N-methyl-piperazine, the title compound, m.p. 206°–207° C., was obtained in 60% yield.

EXAMPLE 5

2-Cyano-3-(6'-methylergoline-8'β)-N-ethylpropionamide (355/1138) (I: $R_1$=CH$_3$CH$_2$NH, $R_3$=CN, $R_4$=CH$_3$, $R_2$=$R_5$=$R_6$=$R_7$=H)

Operating as in Example 2, but employing sodium N-ethylcyanoacetamide, the title compound, m.p. 225°–226° C., was obtained in 65% yield.

EXAMPLE 6

2-Cyano-3-(6'-methylergoline-8'β)-N-benzylpropionamide (355/1131) (I: $R_1$=C$_6$H$_5$CH$_2$NH, $R_3$=CN, $R_4$=CH$_3$, $R_2$=$R_5$=$R_6$=$R_7$=H)

Operating as in Example 2, but employing sodium N-benzylcyanacetamide, the title compound, m.p. 233°–234° C., was obtained in 75% yield.

EXAMPLE 7

2-Cyano-3-(6'-methylergoline-8'β)-N-propionylpiperidine (I: $R_1$=piperidino, $R_3$=CN, $R_4$=CH$_3$, $R_2$=$R_5$=$R_6$=$R_7$=H)

Operating as in Example 2, but employing sodium cyanoacetylpiperidine, the title compound, m.p. 252°–253° C., was obtained in 77% yield.

EXAMPLE 8

2-Cyano-3-(6'-methylergoline-8'β)-propionamide (355/1057) (I: $R_1$=NH$_2$, $R_3$=CN, $R_4$=CH$_3$, $R_2$=$R_5$=$R_6$=$R_7$=H)

Operating as in Example 2, but employing sodium cyanoacetamide, the title compound, m.p. 248°–250° C., was obtained in 45% yield.

EXAMPLE 9

2-Cyano-3-(6'-ethylergoline-8'β)-propionamide (I: $R_1$=NH$_2$, $R_3$=CN, $R_4$=C$_2$H$_5$, $R_2$=$R_5$'$R_6$=$R_7$=H)

Operating as Example 8, but employing 6-ethyl-8β-tosyloxymethylergoline, the title compound was obtained in 42% yield, m.p. 243°–245° C.

EXAMPLE 10

2-Cyano-3-(6'-allylergoline-8'β)-propionamide (I: $R_1$=NH$_2$, $R_3$=CN, $R_4$=allyl, $R_2$=$R_5$=$R_6$=$R_7$=H)

Operating as in Example 8, but employing 6-allyl-8β-tosyloxymethylergoline, the title compound was obtained in 40% yield.

EXAMPLE 11

2-Cyano-3-(6'-methylergoline-8'β)-N-propionylpyrrolidine (355/1133) (I: $R_1$=1-pyrrolidinyl, $R_3$=CN, $R_4$=CH$_3$, $R_2$=$R_5$=$R_6$=$R_7$=H)

Operating as in Example 2, but employing sodium cyanoacetylpyrrolidine, the title compound, m.p. 219°–220° C., was obtained in 68% yield.

EXAMPLE 12

2-Cyano-3-(1',6'-dimethylergoline-8'β)-propionamide (I: $R_1$=NH$_2$, $R_3$=CN, $R_4$=$R_7$=CH$_3$, $R_2$=$R_5$=$R_6$=H)

Operating as in Example 8, but employing 1,6-dimethyl-8β-tosyloxymethylergoline, the title compound, m.p. 196°–197° C., is obtained in 80% yield.

EXAMPLE 13

2-Cyano-3-(6'-methyl-10'-methoxyergoline-8'β)-propionamide (I: $R_1$=NH$_2$, $R_3$=CN, $R_4$=CH$_3$, $R_5$=CH$_3$O, $R_2$=$R_6$=$R_7$=H)

Operating as in Example 8, but employing 6-methyl-10-methoxy-8β-tosyloxymethylergoline, the title compound m.p. 207°–208° C., was obtained in 45% yield.

EXAMPLE 14

2-Cyano-3-(1',6'-dimethyl-10'-methoxyergoline-8'β)-propionamide (I: $R_1$=NH$_2$, $R_3$=CN, $R_4$=$R_7$=CH$_3$, $R_5$=CH$_3$O, $R_2$=$R_6$=H)

Operating as in Example 8, but employing 1,6-dimethyl-10-methoxy-8β-tosyloxymethylergoline, the title compound, m.p. 238°–240° C., was obtained in 81% yield.

EXAMPLE 15

2-Cyano-3-(2'-bromo-6'-methylergoline-8'β)-propionamide (355/1139) (I: $R_1$=NH$_2$, $R_3$=CN, $R_4$=CH$_3$, $R_6$=Br, $R_2$=$R_5$=$R_7$=H)

Operating as in Example 8, but employing 2-bromo-6-methyl-8β-tosyloxymethylergoline, the title compound, m.p. 171°–173° C., was obtained in 41% yield.

EXAMPLE 16

2-Acetyl-3-(6'-methylergoline-8'β)-propionic acid ethyl ester (I: $R_1$—OCH$_2$CH$_3$, $R_3$=CH$_3$CO, $R_4$=CH$_3$, $R_2$=$R_5$=$R_6$=$R_7$=H)

Operating as in Example 1, but employing sodium ethyl acetoacetate, the title compound, m.p. 178°–179° C., was obtained in 70% yield.

EXAMPLE 17

3-Acetyl-4-(6'-methylergoline-8'β)-butanone (I: $R_1=R_4=CH_3$, $R_3=CH_3CO$, $R_2=R_5=R_6=R_7=H$)

Operating as in Example 1, but employing sodium acetylacetone, the title compound, m.p. 210°–212° C., was obtained in 75% yield.

EXAMPLE 18

2-Cyano-2-ethyl-3-(6'-methylergoline-8'β)-propionamide (I: $R_1=NH_2$, $R_2=C_2H_5$, $R_3=CN$, $R_4=CH_3$, $R_5=R_6=R_7=H$)

Operating as in Example 8, but employing sodium ethylcyanoacetamide, the title compound, m.p. 217° C., was obtained in 43% yield.

EXAMPLE 19

2-Cyano-2-phenyl-3-(6'-methylergoline-8'β)-propionamide (I: $R_1=NH_2$, $R_2=C_6H_5$, $R_3=CN$, $R_4=CH_3$, $R_5=R_6=R_7=H$)

Operating as in Example 8, but employing sodium phenylcyanoacetamide, the title compound, m.p. 232° C., was obtained in 45% yield.

EXAMPLE 20

2-Cyano-3-(1',6'-dimethylergoline-8'β)-N-ethylpropionamide

Operating as in Example 5, but employing 1,6-dimethyl-8β-tosyloxymethylergoline, the title compound, m.p. 194°–196° C., is obtained in 60% yield.

EXAMPLE 21

2-Cyano-3-(1',6'-dimethylergoline-8'β)-N-propionylpyrrolidine

Operating as in Example 11, but employing 1,6-dimethyl-8β-tosyloxymethylergoline, the title compound, m.p. 207°–209° C., is obtained in 55% yield.

EXAMPLE 22

2-Cyano-3-(1',6'-dimethylergoline-8'β)-N-benzylpropionamide

Operating as in Example 6, but employing 1,6-dimethyl-8β-tosyloxymethylergoline, the title compound, m.p. 175°–177° C., is obtained in 40% yield.

EXAMPLE 23

2-Methylsulfonyl-3-(6'-methylergoline-8'β)-propionic acid ethyl ester

Operating as in Example 1, but employing sodium ethylmethylsulfonyl acetate, the title compound, m.p. 199°–201° C., is obtained in 70% yield.

EXAMPLE 24

2-Methylsulfonyl-3-(6'-methylergoline-8'β)-N-benzylpropionamide

Operating as in Example 2, but employing sodium N-benzylmethylsulfonylacetamide, the title compound, m.p. 285°–287° C., is obtained in 60% yield.

EXAMPLE 25

2-Methylsulfonyl-3-(6'-methylergoline-8'β)-propionamide

Operating as in Example 2, but employing sodium methylsulfonylacetamide, the title compound, m.p. 242°–244° C., is obtained in 65% yield.

EXAMPLE 26

2-Methylsulfonyl-3-(6'-methylergoline-8'β)-N-propionylpyrrolidine

Operating as in Example 2, but employing sodium methylsulfonylacetylpyrrolidine, the title compound, m.p. 235°–237° C., is obtained in 69% yield.

EXAMPLE 27

2-Methylsulfonyl-3-(6'-methylergoline-8'β)-N-ethylpropionamide

Operating as in Example 2, but employing sodium N-ethylmethylsulphonylacetamide, the title compound, m.p. 227°–229° C., is obtained in 60% yield.

EXAMPLE 28

2-Acetyl-3-(6'-methylergoline-8'β)-propionamide

Operating as in Example 2, but employing sodium acetylacetamide, the title compound, m.p. 225°–227° C., is obtained in 40% yield.

EXAMPLE 29

2-Cyano-3-(2'-chloro-6'-methylergoline-8'β)-propionamide

Operating as in Example 8, but employing 2-chloro-6-methyl-8β-tosyloxymethylergoline, the title compound, m.p. 245°–246° C., is obtained in 45% yield.

What is claimed is:

1. A compound of formula (I):

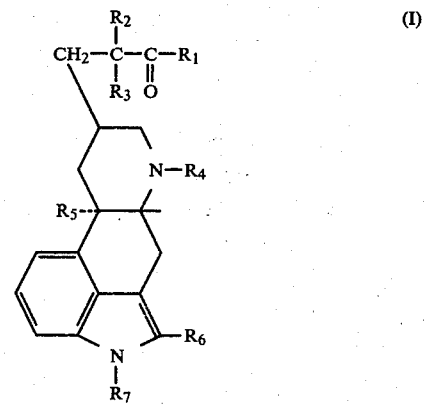

wherein
$R_1$ represents a methyl, phenyl, piperidino, 1-pyrrolidinyl, morpholino or 4-methyl-1-piperazinyl group, an alkyl or alkoxy group having from 1 to 4 carbon atoms, an amino group, a substituted amino group of the formula NHR' (wherein R' represents an alkyl group having from 1 to 4 carbon atoms, a cycloalkyl group, a benzyl group, or a phenyl group) or a substituted amino group of the formula NR"R''' (wherein R" and R''' both represent alkyl groups having from 1 to 4 carbon atoms);

$R_2$ represents a hydrogen atom, an alkyl group having from 1 to 4 carbon atoms, or a phenyl group;

$R_3$ represents a fluorine atom, a cyano, difluoromethyl, difluorobromomethyl, trifluoromethyl, methylthio, methylsulphonyl, or sulphonamido group, an alkoxy group having from 1 to 4 carbon atoms, an alkanoyl group having from 2 to 5 carbon atoms, or a benzoyl group;

$R_4$ represents methyl, ethyl, or allyl;

$R_5$ represents a hydrogen atom or a methoxy group;

$R_6$ represents a hydrogen or halogen atom or a methyl group; and $R_7$ represents a hydrogen atom or a methyl group.

2. A compound as defined in claim 1, which is 2-cyano-3-(6'-methylergoline-8'β)-N-ethylpropionamide.

3. A compound as defined in claim 1, which is 2-cyano-3-(6'-methylergoline-8'β)-N-benzylpropionamide.

4. A compound as defined in claim 1, which is 2-cyano-3-(6'-methylergoline-8'β)-propionamide.

5. A compound as defined in claim 1, which is 2-cyano-3-(6'-methylergoline-8'β)-N-propionylpyrrolidine.

6. A compound as defined in claim 1, which is 2-cyano-3-(2'-bromo-6'-methylergoline-8'β)-propionamide.

7. A compound as defined in claim 1, which is 2-cyano-3-(6'-methylergoline-8'β)propionic acid ethyl ester.

8. A compound as defined in claim 1, which is 2-cyano-3-(6'-methylergoline-8'β)-N-propionylmorpholine.

9. A compound as defined in claim 1, which is 2-cyano-3-(6'-methylergoline-8'β)-N-phenylpropionamide.

10. A compound as defined in claim 1, which is 2-cyano-3-(6'-methylergoline-8'β)-N-propionyl (N'-methyl)piperazine.

11. A compound as defined in claim 1, which is 2-cyano-3-(6'-methylergoline-8'β)-N-propionylpiperidine.

12. A compound as defined in claim 1, which is 2-cyano-3-(6'-ethylergoline-8'β)-propionamide.

13. A compound as defined in claim 1, which is 2-cyano-3-(6'-allylergoline-8'β)-propionamide.

14. A compound as defined in claim 1, which is 2-cyano-3-(1',6'-dimethylergoline-8'β)-propionamide.

15. A compound as defined in claim 1, which is 2-cyano-3-(6'-methyl-10'-methoxyergoline-8'β)-propionamide.

16. A compound as defined in claim 1, which is 2-cyano-3-(1',6'-dimethyl-10'-methoxyergoline-8'β)-propionamide.

17. A compound as defined in claim 1, which is 2-acetyl-3-(6'-methylergoline-8'β)-propionic acid ethyl ester.

18. A compound as defined in claim 1, which is 3-acetyl-4-(6'-methylergoline-8'β)-butanone.

19. A compound as defined in claim 1, which is 2-cyano-2-ethyl-3-(6'-methylergoline-8'β)-propionamide.

20. A compound as defined in claim 1, which is 2-cyano-2-phenyl-3-(6'-methylergoline-8'β)-propionamide.

21. A compound as defined in claim 1, which is 2-cyano-3-(1',6'-dimethylergoline-8'β)-N-ethylpropionamide.

22. A compound as defined in claim 1, which is 2-cyano-3-(1',6'-dimethylergoline-8'β)-N-propionylpyrrolidine.

23. A compound as defined in claim 1, which is 2-cyano-3-(1',6'-dimethylergoline-8'β)-N-benzylpropionamide.

24. A compound as defined in claim 1, which is 2-methylsulfonyl-3-(6'-methylergoline-8'β)-propionic acid ethyl ester.

25. A compound as defined in claim 1, which is 2-methylsulfonyl-3-(6'-methylergoline-8'β)-N-benzylpropionamide.

26. A compound as defined in claim 1, which is 2-methylsulfonyl-3-(6'-methylergoline-8'β)-propionamide.

27. A compound as defined in claim 1, which is 2-methylsulfonyl-3-(6'-methylergoline-8'β)-N-propionylpyrrolidine.

28. A compound as defined in claim 1, which is 2-methylsulfonyl-3-(6'-methylergoline-8'β)-N-ethylpropionamide.

29. A compound as defined in claim 1, which is 2-acetyl-3-(6'-methylergoline-8'β)-propionamide.

30. A compound as defined in claim 1, which is 2-cyano-3-(2'-chloro-6'-methylergoline-8'β)-propionamide.

* * * * *

UNITED STATES PATENT AND TRADEMARK OFFICE
CERTIFICATE OF CORRECTION

PATENT NO. : 4,252,941

DATED : February 24, 1981

INVENTOR(S) : Sergio MANTEGANI; Giuliana ARCARI; Anna Maria CARAVAGGI; Germano BOSISIO It is certified that error appears in the above-identified patent and that said Letters Patent are hereby corrected as shown below:

Title page under "OTHER PUBLICATIONS", the word "Farmerco" should read --Farmaco--.

Column 2, line 19, the value "C." should read --C--.

Signed and Sealed this

Twenty-third Day of June 1981

[SEAL]

Attest:

RENE D. TEGTMEYER

*Attesting Officer*    *Acting Commissioner of Patents and Trademarks*

UNITED STATES PATENT AND TRADEMARK OFFICE
CERTIFICATE OF CORRECTION

PATENT NO. : 4,252,941

DATED : February 24, 1981

INVENTOR(S) : Mantegani et al.

It is certified that error appears in the above—identified patent and that said Letters Patent is hereby corrected as shown below:

In the Abstract, in Formula (I) please insert the symbol -- ▼H -- in position 5 of the A ring, as shown below.

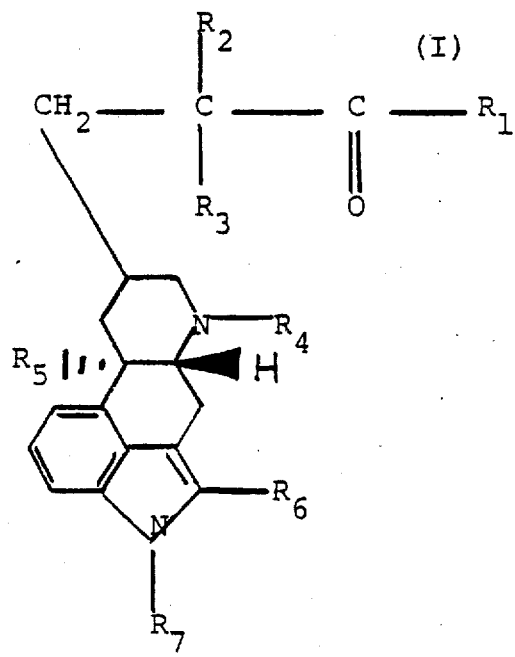

In column 1, in Formula (I) please insert the symbol -- ▼H -- in position 5 of the A ring, as shown above.

In column 2, in Formula (II) please insert the symbol -- ▼H -- in position 5 of the A ring, as shown below.

UNITED STATES PATENT AND TRADEMARK OFFICE
CERTIFICATE OF CORRECTION

PATENT NO. : 4,252,941

DATED : February 24, 1981

INVENTOR(S) : Mantegani et al.

It is certified that error appears in the above—identified patent and that said Letters Patent is hereby corrected as shown below:

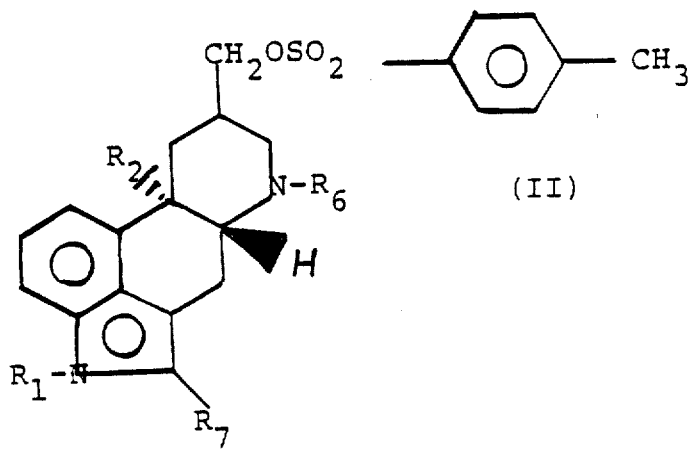

In column 8, in Formula (I), please insert the symbol -- ▼H -- in position 5 of the A ring, as shown above.

Signed and Sealed this

Thirteenth Day of April 1982

[SEAL]

Attest:

GERALD J. MOSSINGHOFF

Attesting Officer    Commissioner of Patents and Trademarks